United States Patent
Ravishankar et al.

(10) Patent No.: US 10,647,629 B2
(45) Date of Patent: May 12, 2020

(54) OLIGOMERIZATION PROCESS INVOLVING CRYSTALLINE MOLECULAR SIEVE

(71) Applicant: HINDUSTAN PETROLEUM CORPORATION LTD., Mumbai (IN)

(72) Inventors: Raman Ravishankar, Karnataka (IN); Bennet Chelliahn, Karnataka (IN); Ragireddy Sudarshan Reddy, Karnataka (IN); Peddy Venkat Chalapathy Rao, Karnataka (IN); Gandham Sriganesh, Karnataka (IN)

(73) Assignee: Hindustan Petroleum Corporation Limited, Mumbai (IN)

( * ) Notice: Subject to any disclaimer, the term of this patent is extended or adjusted under 35 U.S.C. 154(b) by 0 days.

(21) Appl. No.: 16/095,483

(22) PCT Filed: Feb. 1, 2017

(86) PCT No.: PCT/IN2017/050047
§ 371 (c)(1),
(2) Date: Oct. 22, 2018

(87) PCT Pub. No.: WO2018/096551
PCT Pub. Date: May 31, 2018

(65) Prior Publication Data
US 2019/0127293 A1  May 2, 2019

(30) Foreign Application Priority Data
Nov. 25, 2016  (IN) .............................. 201621040380

(51) Int. Cl.
*C07C 2/12* (2006.01)
*B01J 21/04* (2006.01)
*B01J 29/70* (2006.01)
*B01J 35/10* (2006.01)

(52) U.S. Cl.
CPC ................ *C07C 2/12* (2013.01); *B01J 21/04* (2013.01); *B01J 29/7026* (2013.01); *B01J 35/1066* (2013.01); *C07C 2521/04* (2013.01); *C07C 2529/70* (2013.01)

(58) Field of Classification Search
None
See application file for complete search history.

(56) References Cited

U.S. PATENT DOCUMENTS

| | | | |
|---|---|---|---|
| 5,134,243 A | 7/1992 | Bhore et al. | |
| 7,112,711 B2 | 9/2006 | Mathys et al. | |
| 8,716,542 B2 | 5/2014 | Brown et al. | |
| 2004/0133053 A1* | 7/2004 | Martens ................... | C07C 1/20 585/327 |
| 2005/0049448 A1 | 3/2005 | Loescher et al. | |

(Continued)

OTHER PUBLICATIONS

International Search Report, dated Aug. 11, 2017 (PCT/IN2017/050047).

*Primary Examiner* — Ali Z Fadhel
(74) *Attorney, Agent, or Firm* — Robert L. Stearns; Dickinson Wright PLLC (57) ABSTRACT

A process for oligomerization of olefins includes contacting a feedstock with a zeolite catalyst under conditions of oligomerization at pressure between 8-20 bars and temperature in the range of 60-100° C. to obtain oligomers, wherein, the zeolite catalyst has a pentagonal sheet morphology.

17 Claims, 3 Drawing Sheets

(56) References Cited

U.S. PATENT DOCUMENTS

2008/0039669 A1\* 2/2008 Brown .................... B01J 29/06
585/514
2015/0158786 A1\* 6/2015 Mertens .................. B01J 20/08
585/518

\* cited by examiner

OLIGOMERIZATION PROCESS INVOLVING CRYSTALLINE MOLECULAR SIEVE

BACKGROUND

The present disclosure generally relates to a process for oligomerization of olefins, and in particular to a process for the oligomerization of olefins employing zeolite catalyst to obtain higher molecular weight oligomers under milder reaction conditions.

RELATED ART

Olefins, in general are widely used as a valuable feedstock for gasoline blending. Olefins may vary in size, degree of branching, and position of the double bond depending on the source from which they are produced. Olefins constitute an important part of fuel blends. Fuel blending is assuming great significance because of its ability to help cater to the ever-increasing fuel demand. Fuel blending which involves adding varying amounts of alternative fuel to conventional fuel, reduces petroleum consumption. Fuel blending is thus one of the important ways in which we can delay the prospect of a severe petroleum shortage that the world stares at. However, to meet the fuel blending requirements, such as octane rating, vapor pressure requirements, the smaller olefin molecules need to be lengthened to longer chain molecules. One of the most commonly used methods of elongating smaller olefin molecules is an oligomerization reaction. Apart from the aforementioned applications in the fuel industry, higher olefins obtained by oligomerization process also find utility as comonomers in olefin copolymerization. Thus, given its industrial significance, olefin oligomerization process, as a field of research has been abuzz with activity.

Oligomerization reactions generally involve contacting an olefin with a catalyst, resulting in a longer chain molecule. The products of oligomerization are usually mixtures of, olefin dimers, trimers, and higher oligomers.

In the present state of the art, oligomerization reaction requires high temperature and high pressure conditions, which in turn increases operational complications and risk of an accident. Additionally, these conditions also result in poor yield of the oligomer product. There have been attempts to overcome some of the aforementioned drawbacks, by using zeolite catalysts. Zeolite catalyst have been shown to the increase the yield of the oligomer product. However, the catalyst loses its activity rapidly and regeneration of the same involves use of expensive techniques.

U.S. Pat. No. 5,134,243 discloses in the background section that while low temperature oligomerization, i.e., below 200° C., is known, these catalysts have not exhibited sufficient activity at lower temperatures to be viable for industrial applications. It further discloses that the low temperature oligomerization can be selective to produce incremental oligomers, such as, C6, C9, C12, etc. These reactions are known to be selective without significant cracking of the desired product; however, the relative inactivity of these catalysts has prevented the successful development of low temperature processes.

U.S. Pat. No. 7,112,711 relates to a process for oligomerizing alkene having from 3 to 6 carbon atoms by contacting a feedstock including one or several alkene having x carbon atoms, and, b) optionally, one or several alkene having y carbon atoms, x and y being different, with a catalyst containing a zeolite of the MFS structure type. However, the oligomerization reaction is performed at very high temperature and very high pressure conditions, i.e., supercritical conditions, which is not safe and very feasible, especially for industrial scale applications.

U.S. Pat. No. 8,716,542 discloses a process for oligomerizing an olefinic hydrocarbon feedstock comprising at least about 65 wt % olefins including contacting the feedstock with a catalyst composition comprising a TON structure molecular sieve catalyst followed by contacting with a catalyst composition comprising an MFS structure molecular sieve catalyst. It is very clear that the patent application utilizes two structurally different catalyst composition in two different steps. As mentioned above, high severity on the catalyst generally leads to loss of activity and regeneration of the same proves quite expensive. Further, the process was performed at high temperature and high pressure conditions. Additionally, use of two different catalysts in a successive manner makes the process cumbersome.

Specifically, the oligomerization of butenes is often associated with a desire to make a high yield, high quality gasoline product. When oligomerizing butenes, dimerization to $C_8$ products is especially desired with the aim to obtain gasoline range material. However, most of the work that constitutes the prior art has not been able to successfully control the reaction to selectively obtain dimer and trimer. Prior works where the higher oligomerization of butene was carried out using various catalyst have failed to provide high yields and good selectivity specifically for dimerized oligomer.

SUMMARY

Based on the discussion in the preceding paragraphs, it can be seen that there is a critical need for a simple, safe and economical process of oligomerization, with special emphasis on dimer and trimer selectivity. Further, there is also a need for a suitable catalyst for the process of oligomerization to minimize the above mentioned drawbacks.

The present disclosure relates to a process for oligomerization of olefins, said process comprising contacting a feedstock with a zeolite catalyst under conditions of oligomerization at pressure between 8-20 bars and temperature in the range of 60-100° C. to obtain oligomers, wherein, the zeolite catalyst has a pentagonal sheet morphology.

These and other features, aspects and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

BRIEF DESCRIPTION OF DRAWINGS

The detailed description is described with reference to the accompanying figures. In the figures, the left-most digit(s) of a reference number identifies the figure in which the reference number first appears. The same numbers are used throughout the drawings to reference like features and components.

DETAILED DESCRIPTION

Those skilled in the art will be aware that the present disclosure is subject to variations and modifications other than those specifically described. It is to be understood that the present disclosure includes all such variations and modifications. The disclosure also includes all such steps, features, compositions and compounds referred to or indicated in this specification, individually or collectively and any and all combinations of any or more of such steps or features.

Definitions

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. Throughout this specification, unless the context requires otherwise the word "comprise", and variations, such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

The term "zeolite catalyst" and "crystalline molecular sieve" can be used interchangeably.

The term "between" should be understood as being inclusive of the limits.

The term "aliphatic" refers to substituted or unsubstituted saturated alkane chain having from 1 to 10 carbon atoms, substituted or unsubstituted alkene chain having from 1 to 10 carbon atoms.

As used herein, "alkane" groups include saturated hydrocarbons having one or more carbon atoms, including straight-chain alkyl groups, such as methane, ethane, propane, butane, pentane and the like.

As used herein, "alkene" refers to an aliphatic hydrocarbon radical which can be straight or branched, containing at least one carbon-carbon double bond. Examples of alkene groups include, but are not limited to, ethene, propene, n-butene, i-butene, 1-butene, 2-butene, 3-methylbut-2-en, n-pentene, heptene, octene, decene, and the like.

Ratios, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a temperature range of about 120° C. to about 150° C. should be interpreted to include not only the explicitly recited limits of about 120° C. to about 150° C., but also to include sub-ranges, such as 125° C. to 145° C., 130° C. to 150° C., and so forth, as well as individual amounts, including fractional amounts, within the specified ranges, such as 122.2° C., 140.6° C., and 141.3° C., for example.

As discussed above, oligomerization of olefins at optimized conditions without affecting the selectivity of the oligomers obtained is a challenging task. Attempts in the prior art that have been made towards obtaining an improved yield and a high selectivity of the oligomer products involving the use of supercritical reaction conditions or using various catalyst in high amount. The former approach involves an increased risk of accidents and has in general, resulted in the decreased selectivity of the required oligomer, whereas the later approach has proven to be expensive and hence not suitable on an industrial scale. Thus, as a solution to the above mentioned disadvantages, the present disclosure provides a safe and economical process for oligomerization of olefins using a zeolite catalyst to obtain heavier hydrocarbons, having diverse applications.

The present disclosure provides a process for the preparation of oligomers using olefinic feedstock in presence of solid acid catalyst ZSM 57 having pentagonal sheet morphology, which selectively yields higher amounts of dimerized and trimerized hydrocarbons.

In one embodiment, the present disclosure specifically provides a process for the preparation of oligomers using $C_4$ olefinic feedstock in presence of solid acid catalyst ZSM 57, which selectively produces higher amount of $C_8$ hydrocarbons. Oligomerization of isobutene is important for production of high octane gasoline blending component.

The present disclosure, thus provides process of oligomerization under optimized oligomerization conditions. More specifically, the present disclosure, provides process for olefin oligomerization under optimized conditions using a zeolite catalyst.

In one implementation, the present disclosure relates to a process for oligomerization of olefins, said process comprising contacting a feedstock with a zeolite catalyst under conditions of oligomerization.

In one implementation, the present disclosure relates to a process for oligomerization of olefins, said process comprising contacting a feedstock with a zeolite catalyst under conditions of oligomerization at pressure between 8-20 bars and temperature in the range of 60-100° C. to obtain oligomers, wherein the zeolite catalyst has a pentagonal sheet morphology.

In one implementation, the present disclosure relates to a process for oligomerization of olefins, said process comprising contacting a feedstock with a zeolite catalyst under conditions of oligomerization at pressure between 12-20 bars and temperature in the range of 80-100° C. to obtain oligomers, wherein the zeolite catalyst has a pentagonal sheet morphology.

In one implementation, the present disclosure relates to a process for oligomerization of olefins, said process comprising contacting a feedstock with a zeolite catalyst under conditions of oligomerization at pressure of 16 bars and a temperature of 80° C. to obtain oligomers, wherein the zeolite catalyst has a pentagonal sheet morphology.

In one implementation, the present disclosure relates to a process for oligomerization of olefins, said process comprising contacting a feedstock comprising aliphatic hydrocarbons with a zeolite catalyst under conditions of oligomerization at pressure between 8-20 bars and temperature in the range of 60-100° C. to obtain oligomers, wherein the zeolite catalyst has a pentagonal sheet morphology.

In one implementation, the present disclosure relates to a process for oligomerization of olefins, said process comprising contacting a feedstock comprising aliphatic hydrocarbons having a mixture of at least one alkane and at least one alkene with a zeolite catalyst under conditions of oligomerization at pressure between 8-20 bars and temperature in the range of 60-100° C. to obtain oligomers, wherein the zeolite catalyst has a pentagonal sheet morphology.

In one implementation, the present disclosure relates to a process for oligomerization of olefins, said process comprising contacting a feedstock comprising a mixture of saturated and unsaturated hydrocarbons with a zeolite catalyst under conditions of oligomerization at pressure between 8-20 bars and temperature in the range of 60-100° C. to obtain oligomers, wherein the zeolite catalyst has a pentagonal sheet morphology.

In one implementation, the present disclosure relates to a process for oligomerization of olefins, said process comprising contacting a feedstock comprising a mixture of unsaturated hydrocarbons with a zeolite catalyst under conditions of oligomerization at pressure between 8-20 bars and temperature in the range of 60-100° C. to obtain oligomers, wherein the zeolite catalyst has a pentagonal sheet morphology.

In another implementation, the feedstock may also include other components, such as, aromatic hydrocarbons, sulfur containing compounds, oxides of carbon, such as CO, $CO_2$, methane, ethane, propane or their mixture, and water.

In one implementation, the present disclosure relates to a process for oligomerization of olefins, said process comprising contacting a feedstock comprising aliphatic hydrocarbons having a mixture of at least one alkane and at least one alkene, with a zeolite catalyst under conditions of oligomerization at pressure between 8-20 bars and temperature in the range of 60-100° C. to obtain oligomers, wherein the zeolite catalyst has a pentagonal sheet morphology, and the alkene to alkane weight ratio in the feedstock is in the range of 30:70-70:30.

In one implementation, the present disclosure relates to a process for oligomerization of olefins, said process comprising contacting a feedstock comprising aliphatic hydrocarbons having a mixture of at least one alkane and at least one alkene, with a zeolite catalyst under conditions of oligomerization at pressure between 8-20 bars and temperature in the range of 60-100° C. to obtain oligomers, wherein the zeolite catalyst has a pentagonal sheet morphology, and the alkene to alkane weight ratio is 50:50.

In one implementation, the present disclosure relates to a process for oligomerization of olefins, said process comprising contacting a feedstock comprising aliphatic hydrocarbons having a mixture of at least one alkane and at least one alkene, with a zeolite catalyst under conditions of oligomerization at pressure between 8-20 bars and temperature in the range of 60-100° C. to obtain oligomers, wherein the zeolite catalyst has a pentagonal sheet morphology, and the alkene weight percentage is in the range of 30-70% with respect to the feedstock.

In one implementation, the present disclosure relates to a process for oligomerization of olefins, said process comprising contacting a feedstock comprising aliphatic hydrocarbons having a mixture of at least one alkane and at least one alkene, with a zeolite catalyst under conditions of oligomerization at pressure between 8-20 bars and temperature in the range of 60-100° C. to obtain oligomers, wherein the zeolite catalyst has a pentagonal sheet morphology, and the alkane weight percentage is in the range of 30-70% with respect to the feedstock.

In one implementation, the present disclosure relates to a process for oligomerization of olefins, said process comprising contacting a feedstock comprising aliphatic hydrocarbons having a mixture of $C_1$-$C_{10}$ alkane and $C_2$-$C_{10}$ alkene, with a zeolite catalyst under conditions of oligomerization at pressure between 8-20 bars and temperature in the range of 60-100° C. to obtain oligomers, wherein the zeolite catalyst has a pentagonal sheet morphology.

In one implementation, the present disclosure relates to a process for oligomerization of olefins, said process comprising contacting a feedstock comprising aliphatic hydrocarbons having a mixture of $C_1$-$C_6$ alkane and $C_2$-$C_6$ alkene, with a zeolite catalyst under conditions of oligomerization at pressure between 8-20 bars and temperature in the range of 60-100° C. to obtain oligomers, wherein the zeolite catalyst has a pentagonal sheet morphology.

In one implementation, the present disclosure relates to a process for oligomerization of olefins, said process comprising contacting a feedstock comprising aliphatic hydrocarbons having a mixture of $C_2$-$C_{10}$ alkane and $C_2$-$C_{10}$ alkene, with a zeolite catalyst under conditions of oligomerization at pressure between 8-20 bars and temperature in the range of 60-100° C. to obtain oligomers, wherein the zeolite catalyst has a pentagonal sheet morphology.

In one implementation, the present disclosure relates to a process for oligomerization of olefins, said process comprising contacting a feedstock comprising aliphatic hydrocarbons having a mixture of $C_3$-$C_6$ alkane and $C_3$-$C_6$ alkene, with a zeolite catalyst under conditions of oligomerization at pressure between 8-20 bars and temperature in the range of 60-100° C. to obtain oligomers, wherein the zeolite catalyst has a pentagonal sheet morphology.

In another implementation, the oligomer is formed due to dimerization and trimerization of at least one alkene.

In one implementation, the present disclosure relates to a process for oligomerization of olefins, said process comprising contacting a feedstock with a ZSM 57 under conditions of oligomerization at pressure between 8-20 bars and temperature in the range of 60-100° C. to obtain oligomers, wherein the zeolite catalyst has a pentagonal sheet morphology.

In another implementation, the present disclosure relates to a process for oligomerization of olefins using zeolite catalyst ZSM 57, wherein the catalyst can be regenerated in a very cost effective manner.

In one implementation, the present disclosure relates to a process for oligomerization of olefins, said process comprising contacting a feedstock with a ZSM 57 under conditions of oligomerization at pressure between 8-20 bars and temperature in the range of 80-100° C. to obtain oligomers, wherein the zeolite catalyst has a pentagonal sheet morphology.

In one implementation, the present disclosure relates to a process for oligomerization of olefins, said process comprising contacting a feedstock with a zeolite catalyst loaded on alumina extrudes under conditions of oligomerization at pressure between 8-20 bars and temperature in the range of 60-100° C. to obtain oligomers, wherein the zeolite catalyst has a pentagonal sheet morphology.

In one implementation, the present disclosure relates to a process for oligomerization of olefins, said process comprising contacting a feedstock with a ZSM 57 loaded on alumina extrudates under conditions of oligomerization at pressure between 8-20 bars and temperature in the range of 60-100° C. to obtain oligomers, wherein the zeolite catalyst has a pentagonal sheet morphology.

In one implementation, the present disclosure relates to a process for oligomerization of olefins, said process comprising contacting a feedstock with a ZSM 57 loaded on alumina extrudates under conditions of oligomerization at pressure between 8-20 bars and temperature in the range of 60-100° C. to obtain oligomers, wherein the zeolite catalyst has a pentagonal sheet morphology, and the zeolite catalyst has a ZSM-57 to alumina extrudates ratio in the range of 20:80-60:40.

In one implementation, the present disclosure relates to a process for oligomerization of olefins, said process comprising contacting a feedstock with a ZSM 57 loaded on alumina extrudates under conditions of oligomerization at pressure between 8-20 bars and temperature in the range of 60-100° C. to obtain oligomers, wherein the zeolite catalyst has a pentagonal sheet morphology, and the zeolite catalyst has a ZSM-57 to alumina extrudates ratio of 40:60.

In one implementation, the present disclosure relates to a process for oligomerization of olefins, said process comprising contacting a feedstock with a zeolite catalyst under conditions of oligomerization at pressure between 8-20 bars and temperature in the range of 60-100° C. at a weight hourly space velocity (WHSV) in the range of 1-4 $h^{-1}$ to obtain oligomers, wherein the zeolite catalyst has a pentagonal sheet morphology.

In one implementation, the present disclosure relates to a process for oligomerization of olefins, said process comprising contacting a feedstock with a zeolite catalyst under conditions of oligomerization at pressure between 8-20 bars and temperature in the range of 60-100° C. at a weight hourly space velocity (WHSV) in the range of 1-4 $h^{-1}$ and at an olefin space velocity in the range of 1-4 $h^{-1}$ to obtain oligomers, wherein the zeolite catalyst has a pentagonal sheet morphology.

In one implementation, the present disclosure relates to a process for oligomerization of olefins, said process comprising contacting a feedstock with a zeolite catalyst under conditions of oligomerization at pressure between 8-20 bars and temperature in the range of 60-100° C. to obtain oligomers, wherein the zeolite catalyst has a pentagonal sheet morphology, wherein the olefin percentage conversion is in the range of 35-92%, based on the alkene weight in the feedstock.

In one implementation, the present disclosure relates to a process for oligomerization of olefins, said process comprising contacting a feedstock with a zeolite catalyst under conditions of oligomerization at pressure between 8-20 bars and temperature in the range of 60-100° C. to obtain oligomers, wherein the zeolite catalyst has a pentagonal sheet morphology, wherein the oligomerization selectivity for the dimerization product is up to 92%.

In one implementation, the present disclosure relates to a process for oligomerization of olefins, said process comprising contacting a feedstock comprising aliphatic hydrocarbons having a mixture of at least one alkane and at least one alkene, with a zeolite catalyst under conditions of oligomerization at pressure between 8-20 bars and temperature in the range of 60-100° C. to obtain oligomers, wherein, the zeolite catalyst has a pentagonal sheet morphology, wherein the alkene is a mixture of butenes and the oligomer product is a mixture of octenes and dodecenes and the octene selectivity is up to 92%.

In one implementation, the butenes can be selected from 1-butene, 2-butene, n-butene, i-butene and the like and combinations thereof.

In one implementation, the present disclosure relates to a process for oligomerization of olefins, said process comprising contacting a feedstock comprising a mixture of C4 alkane and alkene with ZSM 57 loaded on alumina extrudates under conditions of oligomerization at pressure between 8-20 bars and temperature in the range of 60-100° C. at a weight hourly space velocity (WHSV) in the range of 1-4 $h^{-1}$ and at an olefin space velocity in the range of 1-4 $h^{-1}$ to obtain oligomers, wherein the zeolite catalyst has a pentagonal sheet morphology, wherein the oligomer is a $C_8$ hydrocarbon.

In one implementation, the present disclosure relates to a process for oligomerization of olefins, said process comprising contacting a feedstock comprising a mixture of C4 alkane and alkene with ZSM 57 loaded on alumina extrudates under conditions of oligomerization at pressure between 8-20 bars and temperature in the range of 60-100° C. at a weight hourly space velocity (WHSV) in the range of 1-4 $h^{-1}$ and at an olefin space velocity in the range of 1-4 $h^{-1}$ to obtain oligomers, wherein the zeolite catalyst has a pentagonal sheet morphology, and the oligomer is a $C_{12}$ hydrocarbon.

EXAMPLES

The disclosure will now be illustrated with working examples, which is intended to illustrate the working of disclosure and not intended to take restrictively to imply any limitations on the scope of the present disclosure. Other examples are also possible which are within the scope of the present disclosure.

Example 1

Synthesis of ZSM-57

Figure 1:
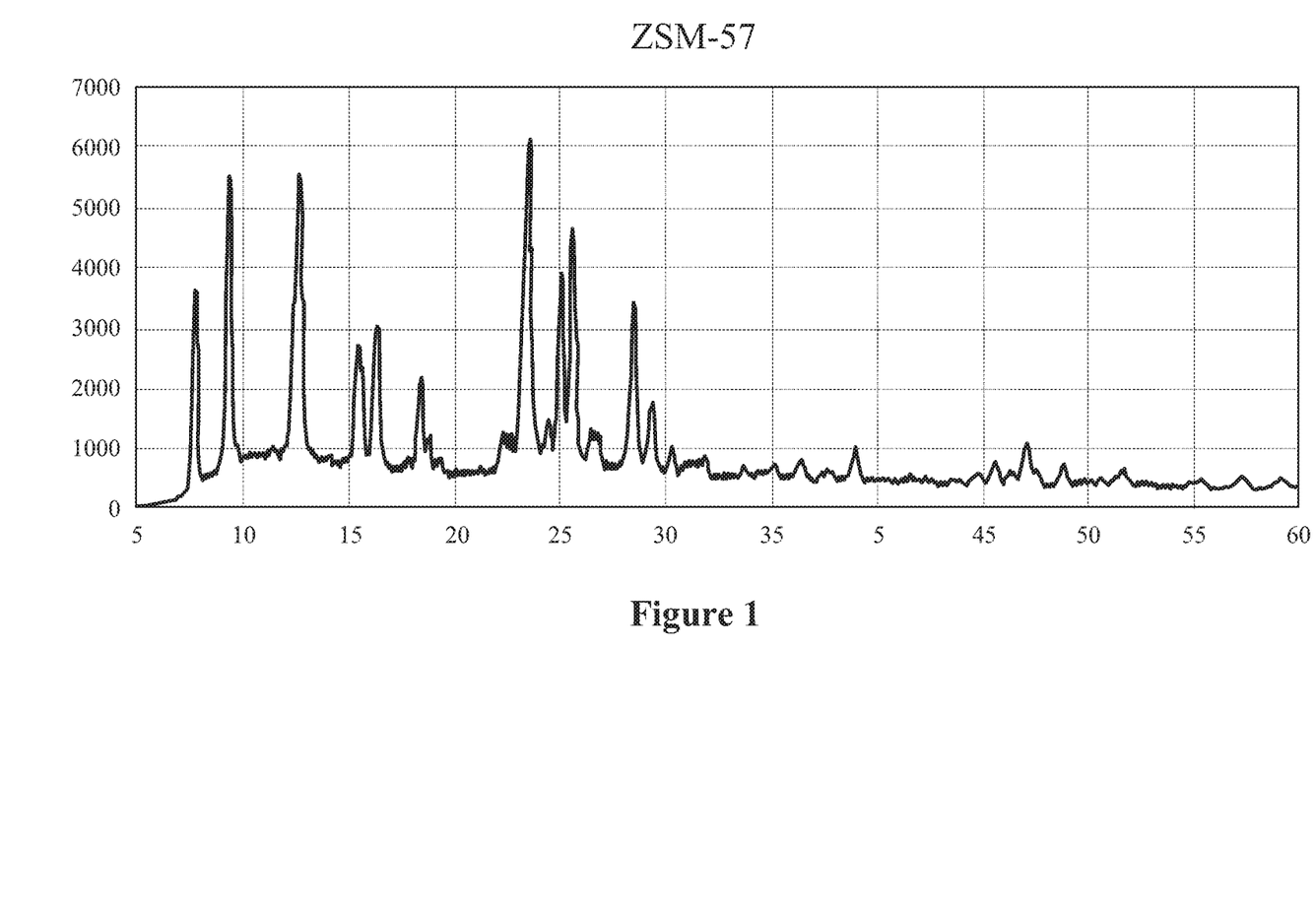
FIG. 1 illustrates the XRD data of ZSM 57 of the present disclosure with pentagonal sheet morphology, wherein the x axis refers to 2 Theta and y axis refers to intensity.

Solution 1 containing 50 g Ludox HS40 (a colloidal silica solution purchased from Sigma-Aldrich as 40 wt % $SiO_2$ in water) was dissolved in 123.5 ml of distilled water and mixed in a beaker. Solution 2 was then prepared by adding 14.21 g of N,N,N,N',N', N'-hexaethylpentanediammonium bromide to 33 mL of distilled water and further added to Solution 1. Solution 3 was made by dissolving 3.72 g $Al_2(SO_4)_3.18H_2O$, 5.416 g NaOH and 33 mL distilled water, and added to the mixture of Solution 1 and Solution 2. The resulting mixture was mixed for an additional 10 minutes, giving a gel with molar composition 2 $Na_2O/R/0.17$ $Al_2O_3/$ 10 $SiO_2/400$ $H_2O$. The gel was transferred to a 600 mL stainless steel autoclave. The autoclave was heated to 160° C. over a period of 2 hours while the mixture was stirred at 100 rpm. Heating at 160° C. and stirring were continued for 144 hours (6 days). As synthesized and calcined at 550° C. samples powder XRD Confirmed as ZSM-57. Morphology of the samples observed as pentagonal sheets of thickness of 75-150 nm. The content of the autoclave was filtered by using Buckner filter and was washed by distilled water until the pH of filtrate was approximately 8. The washed product was dried overnight at 120° C. H-ZSM-57 crystals were synthesized by exchanging with ammonium acetate for thrice at 80° C. for 8 hours. The exchanged ZSM-57 was calcined in air for 8 h at 550° C. in air. Powder XRD studies confirmed (FIG. 1) the structure of ZSM-57. Brunauer-Emmett-Teller (BET) surface area 438.8 $m^2$/gram Comparative Example 1

Solution 1 containing 50 g Ludox HS40 (a colloidal silica solution purchased from Sigma-Aldrich as 40 wt % $SiO_2$ in water) was dissolved in 123.5 ml of distilled water and mixed ina beaker. Solution 2, obtained by addition of 14.21 g of N,N,N,N',N', N'-hexaethylpentanediammonium bromide to 33 mL of distilled water, was added to Solution 1. Solution 3 was made by dissolving 3.72 gr $Al_2(SO_4)_3.18$ $H_2O$, 5.416 g NaOH and 33 mL distilled water and was added to the mixture of Solution 1 and Solution 2. The resulting mixture was mixed for an additional 10 minutes, giving a gel with molar composition 2 $Na_2O/R/0.17$ $Al_2O_3/$ 10 $SiO_2/400$ $H_2O$. The gel was transferred to a 600 ml stainless steel autoclave. The autoclave was heated to 160° C. over a period of 2 hours while the mixture was stirred at 200 rpm. Heating at 160° C. and stirring were continued for 144 hours (6 days). As synthesized and calcined at 550° C., sample's powder XRD confirmed the structure as COK-5. BET surface area was 378.07 m2/gram Comparative Example 2

Solution 1 containing 50 g Ludox HS40 (a colloidal silica solution purchased from Sigma-Aldrich as 40 wt % SiO2 in water) was dissolved in 123.5 mL of distilled water and was mixed in a beaker. Solution 2, obtained by addition of 14.21 g of N,N,N,N',N', N'-hexaethylpentanediammonium bromide to 33 mL of distilled water, was then added to Solution 1. Solution 3 was made by dissolving 3.72 g $Al_2(SO_4)_3.18$ $H_2O$, 5.416 g NaOH and 33 mL distilled water, was added to the mixture of Solution 1 and Solution 2. The resulting mixture was mixed for an additional 10 minutes, giving a gel with molar composition 2 $Na_2O/R/0.17$ $Al_2O_3/10$ $SiO_2/400$ $H_2O$. The gel was transferred to a 600 ml stainless steel autoclave. The autoclave was heated to 160° C. over a period of 2 hours while the mixture was stirred at 120 rpm. Heating at 160° C. and stirring were continued for 168 hours (7 days). As synthesized and calcined at 550° C., sample's powder XRD confirmed it to be COK-5.

Example 1 establishes the criticality of the method of preparation of ZSM 57 of the present disclosure. Further, Comparative Examples 1 and 2 clearly show the importance of the optimized conditions employed in the present disclosure to obtain the zeolite ZSM 57.

From Example 1, it is well appreciated that the optimized process to obtain ZSM 57 of the present disclosure specifically relies on the stirring rate, i.e., stirring speed and time.

Figure 2A:
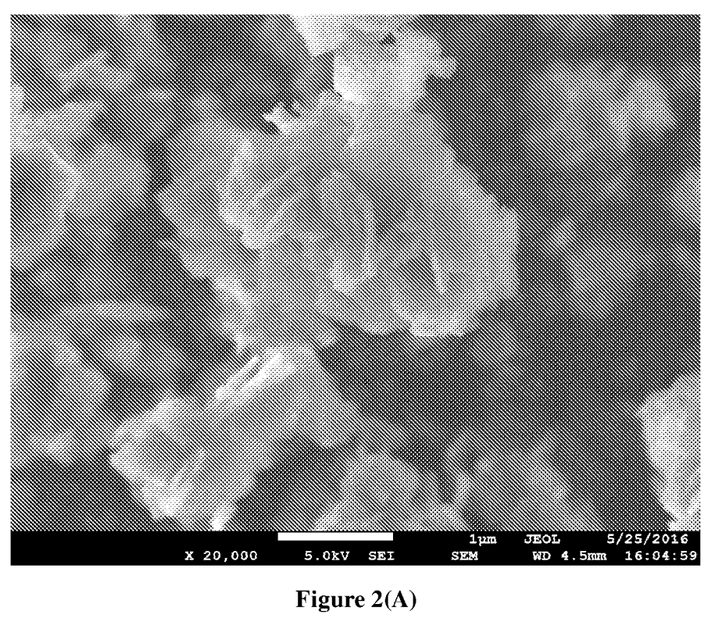
FIG. 2(A) and FIG. 2(B) illustrate SEM images of ZSM 57 of the present disclosure.
Figure 2B:
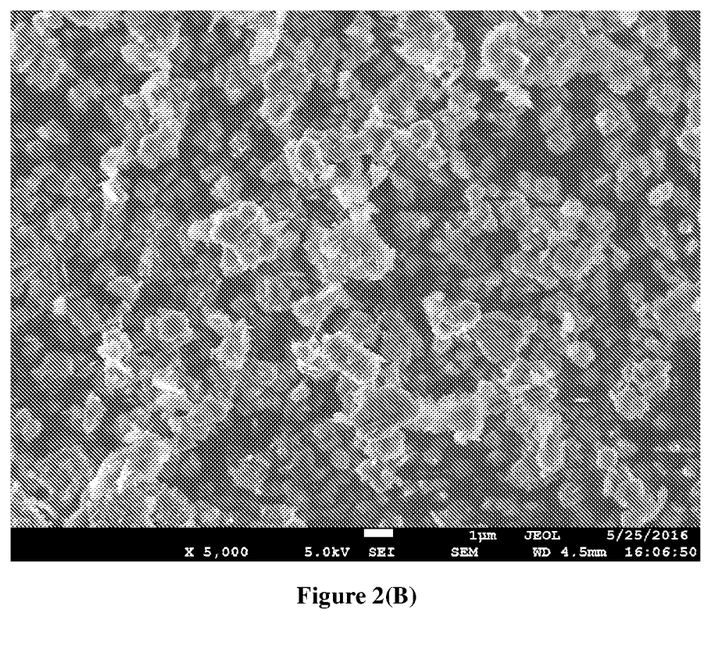

From Comparative Examples 1 and 2, it can be well seen that if any of the aforesaid factors, i.e., stirring speed or stirring time are varied even minutely, it results in an altogether different catalyst. This underscores the significance of process parameters employed while synthesizing the catalyst. Therefore, it clearly shows that the inventors of the present disclosure obtained a catalyst with a specific morphology, pentagonal sheet (FIGS. 2 (A) and (B)) which is responsible for the feasible oligomerization of present disclosure.

Example 2

Formulation of ZSM 57: Alumina Extrudates

Figure 3:
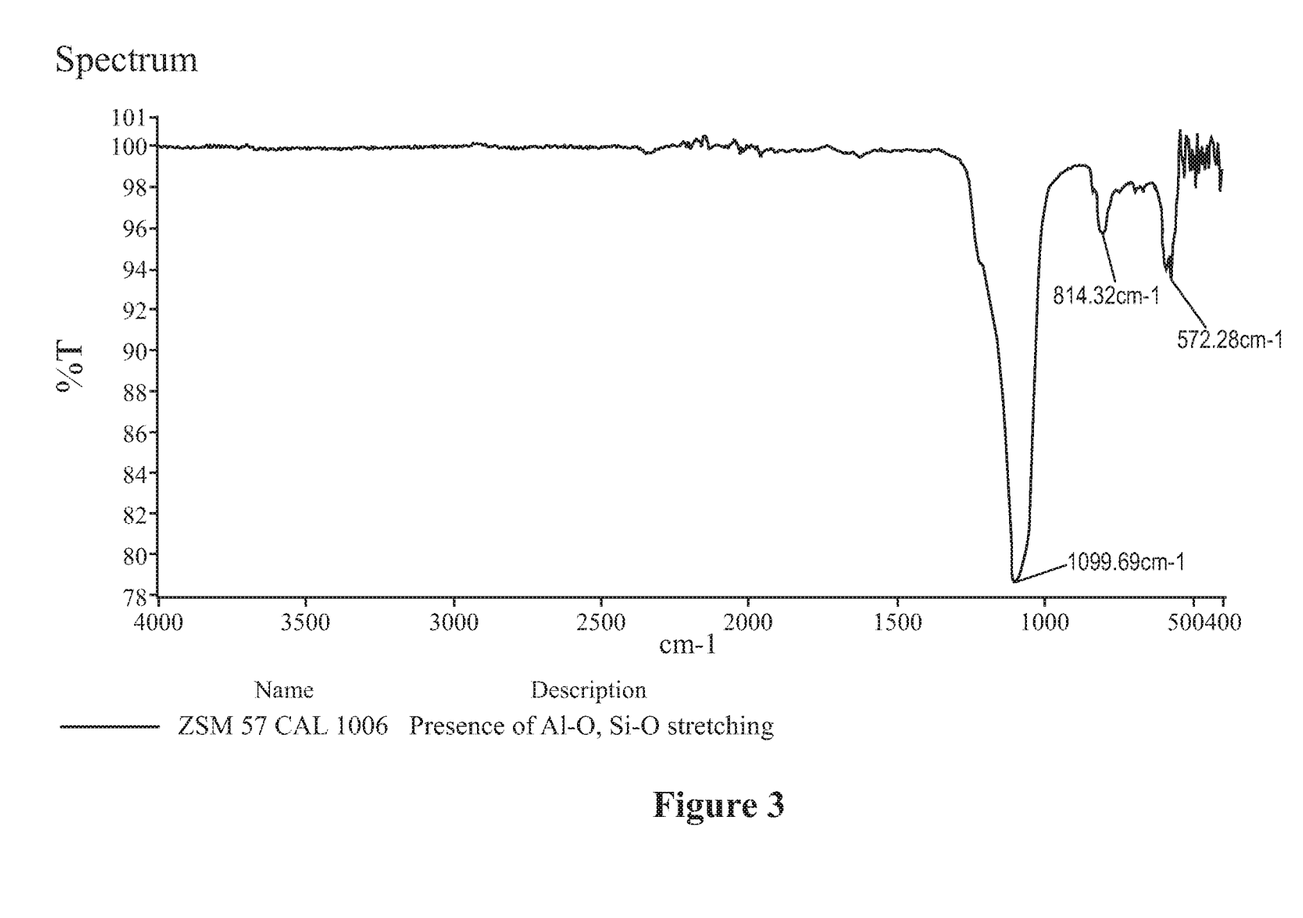
FIG. 3 illustrates the FT-IR spectrum of ZSM 57 loaded on alumina extrudates which clearly shows the presence of Al—O and Si—O stretching peak.

Extrudates of 2 mm size was made in lab scale extruder. Alumina 8 g (40%) was added to H-ZSM-57 12 g (60%) and mechanically mixed. Following this, 0.1 molar nitric acid solution was added to get a wet mixture and the mixture was placed in the lab-scale extruder with 2 mm diameter holes. The wet material was extruded and dried at room temperature overnight (16 hours), followed by 100° C. in an oven for 12 hours. The final dried material (FIG. 3) was calcined at 550° C. for 5 hours in air.

Example 3

Catalyst Operating Conditions

Experiments are conducted by varying process parameters. Table 1 shows that temperature is varied from 60 to 100° C. WHSV is varied in the range of 2 to 3 $hr^{-1}$ and all the experiments are conducted at 16 bar pressure to conduct the reaction in liquid phase for the feed composition of 50 wt % n-butanes/50 wt % i-butylene. The pressure can be varied from 8 to 20 bar according to the feed composition.

Oligomerization over ZSM-57

Feedstock: n-Butane—50% (wt.) and isobutylene—50% (wt.)

Pressure: 16 bars, Hydrogen.

TABLE 1

| Example | Temperature | WHSV ($h^{-1}$) | Olefin SV ($h^{-1}$) |
|---------|-------------|-----------------|----------------------|
| 1 | 60 | 2 | 2.28 |
| 2 | 80 | | |
| 3 | 100 | | |
| 4 | 60 | 3 | 3.41 |
| 5 | 80 | | |
| 6 | 100 | | |

Table 2 shows that the reactions were conducted with molecular sieves/zeolites with varying pore topologies and dimensions at 80° C., 60 bars with WHSV of 2 $h^{-1}$ and the olefin space velocity of 2.28 $h^{-1}$.

TABLE 2

| Example | Zeolite |
|---------|---------|
| 2 | ZSM-57 |
| 7 | ZSM-5 |
| 8 | Ferrrite |
| 9 | Y CBV 720 |
| 10 | Mordenite 1 mm |
| 11 | B-Zeolite |
| 12 | Mordenite 2 mm |

Example 4

Effect of Temperature at Lower Space Velocity

ZSM-57/alumina extrudates in the ratio 40:60 were used to process 50 wt % n-butanes/50 wt % i-butylene feedstock. Reaction conditions were 1600 kPa (16 bar), WHSV 2 $hr^{-1}$ and olefin space velocity 2.28 hr-1 and at 60 to 100° C. feedstock inlet temperature.

TABLE 3

| | Examples | | |
|---|---|---|---|
| | 1 | 2 | 3 |
| Temperature, ° C. | 60 | 80 | 100 |
| Pressure, bar | 16 | 16 | 16 |
| % conversion | 46.0 | 46.8 | 60.6 |
| C8 selectivity | 85.8 | 92 | 65.2 |
| C8 yield | 39.4 | 43.1 | 39.6 |
| C12 yield | 6.6 | 3.7 | 21 |

Observations:

Table 3 shows the overall conversion and selectivity data.

Table 3 shows that the temperature required to maintain approximately 61% of olefin conversion is 100° C.

Table 3 further exemplifies that at 80° C. the C8 selectivity is ~92%. Thus, at 47% conversion the C8 selectivity is more than 92 wt %.

Example 5

Effect of Temperatures at Higher Space Velocity

ZSM-57/alumina extrudates in the ratio 40:60 were used to process 50 wt % n-butanes/50 wt % i-butylene feedstock. Reaction conditions were 1600 kPa (16 bar), WHSV 3 hr$^{-1}$ and olefin space velocity 3.41 hr$^{-1}$ and at 60 to 100° C. feedstock inlet temperature.

TABLE 4

|  | Examples | | |
|---|---|---|---|
|  | 4 | 5 | 6 |
| Temperature, ° C. | 60 | 80 | 100 |
| Pressure, bar | 16 | 16 | 16 |
| % conversion | 35.2 | 40.5 | 49.1 |
| C8 selectivity | 73.8 | 84.6 | 70.4 |
| C8 yield | 26.0 | 34.3 | 34.6 |
| C12 yield | 9.2 | 6.2 | 14.5 |

Table 4 shows the overall conversion and selectivity data. It can be observed that the temperature required to maintain approximately 49% of olefin conversion is 100° C. However, at a temperature of at 85° C., the C8 selectivity is about 85% with 41% conversion.

Table 3 and Table 4 clearly illustrate the importance of low value of space velocity. This is further evidence that the process of oligomerization of the present disclosure is carried out at a very feasible reaction conditions. From the aforesaid tables, it is evident that as the

|  | Examples | | | | | | |
|---|---|---|---|---|---|---|---|
|  | 2 | 7 | 8 | 9 | 10 | 11 | 12 |
| Temperature, ° C. | 80 | 80 | 80 | 80 | 80 | 80 | 80 |
| Pressure, bar | 16 | 16 | 16 | 16 | 16 | 16 | 16 |
| % conversion | 46.8 | 0.8 | 0.2 | 84.9 | 0.4 | 99.8 | 0 |
| C8 selectivity | 92 | 92 | 68.5 | 31 | 0 | 7.6 | 0 |
| C8 yield | 43.1 | 0.73 | 0.118 | 26.3 | 0 | 7.6 | 0 |
| C12 yield | 3.7 | 0.07 | 0.082 | 58.6 | 0.4 | 92.2 | 0 | space velocity increases the conversion and selectivity of the product decreases.

The data provided in the tables above indicate that oligomerization of isobutene has to be carried out in the liquid phase at low temperatures for better product selectivity control due to high exothermicity of the process. The pressure has to be maintained in a way that it is only as high as is required for the reaction to take place in the liquid phase. Space velocity is optimized to get better selectivity towards C8 hydrocarbons as a very low space velocity will give C12+ hydrocarbons and very high space velocity will give less conversion of C4 olefins.

Example 6

Effect of Zeolite Pore Topologies

Table 5 below, shows the effect on the product obtained when the topology of the catalyst was varied.
Table 5
It can be well appreciated from Table 5 that, in Example 2 where the catalyst is ZSM 57 of the present disclosure, the selectivity of C8 oligomer is extraordinarily high. On the other hand, the selectivity of the C8 oligomer decreases as the topology of the catalyst is changed (the catalysts that were used in these examples are defined in Table 2). It is further seen that though ZSM 57 catalyst of the present disclosure does not provide a good yield of $C_{12}$ oligomer, it initiates the process of trimerization of the olefins.

Example 6

Synthesis of $C_8$ Oligomer

A feedstock containing a mixture of butanes and butylenes was contacted with a zeolite catalyst ZSM 57 which is loaded on alumina extrudates under conditions of oligomerization at pressure 16 bars and temperature in the range of 80-100° C. at a weight hourly space velocity (WHSV) of 2-3 h$^{-1}$ and at an olefin space velocity of 2-3 h$^{-1}$ to obtain $C_8$ oligomers. Selectivity for $C_8$ oligomer is more than 90%.

Example 7

Synthesis of $C_{12}$ Oligomer

A feedstock containing a mixture of butanes and butylenes was contacted with a zeolite catalyst ZSM 57 which is loaded on alumina extrudates under conditions of oligomerization at a pressure of 18 bars and a temperature in the range of 80-100° C., at a weight hourly space velocity (WHSV) in the range of 2-3 h$^{-1}$ and an olefin space velocity in the range of 2-3 h$^{-1}$ to obtain $C_{12}$ oligomers. Selectivity of $C_{12}$ oligomer is more than 70%.

Advantages Gained in the Example Illustrative Process in this Subject Matter:

The present disclosure thus provides an economical and safe process for oligomerizing olefins using a zeolite catalyst.

The presence of a pentagonal sheet morphology zeolite catalyst is responsible for the high conversion and selectivity of the process, despite the reaction being carried out at low temperature and pressure.

The present disclosure employs low space velocity value which is responsible for the very high selectivity for the dimeric compound.

Although the subject matter has been described in considerable detail with reference to certain examples and implementations thereof, other implementations are possible. As such, the spirit and scope of the appended claims should not be limited to the description of the preferred examples and implementations contained therein.

We claim:

1. A process for oligomerization of olefins, said process comprising contacting a feedstock comprising the olefins with a zeolite catalyst to oligomerize the olefins at a pressure between 8-20 bars and at a temperature in the range of 60-100° C. to obtain oligomers, wherein, the zeolite catalyst has a pentagonal sheet morphology.

2. The process as claimed in claim 1, wherein the feedstock comprises aliphatic hydrocarbons.

3. The process as claimed in claim 2, wherein the aliphatic hydrocarbons is a mixture of at least one alkane and at least one alkene.

4. The process as claimed in claim 3, wherein the aliphatic hydrocarbons is a mixture of $C_1$-$C_6$ alkane and $C_2$-$C_6$ alkene.

5. The process as claimed in claim 3, wherein the oligomer is formed due to dimerization and trimerization of at least one alkene.

6. The process as claimed in claim 1, wherein the zeolite catalyst is a modified ZSM-57 catalyst produced in a heated autoclave at a temperature of 160° C. and at a stirring rate of 100 rpm.

7. The process as claimed in claim 6, wherein the zeolite catalyst is loaded on alumina extrudates.

8. The process as claimed in claim 7, wherein ZSM-57 to alumina extrudates ratio in the range of 20:80-60:40.

9. The process as claimed in claim 7, wherein ZSM-57 to alumina extrudates ratio of 40:60.

10. The process as claimed in claim 1, wherein the contacting step is carried out at a weight hourly space velocity (WHSV) in the range of 1-4 $h^{-1}$.

11. The process as claimed in claim 5, wherein the contacting step is carried out at an alkene space velocity in the range of 1-4 $h^{-1}$.

12. The process as claimed in claim 5, wherein the alkene percentage conversion is in the range of 35-92%, based on the alkene weight in the feedstock.

13. The process as claimed in claim 5, wherein the oligomerization selectivity for the dimerization product is up to 92%.

14. The process as claimed in claim 3, wherein the at least one alkene to at least one alkane weight ratio in the feedstock is in the range of 30:70-70:30.

15. The process as claimed in claim 3, wherein the alkene weight percentage is in the range of 30-70% with respect to the feedstock.

16. The process as claimed in claim 3, wherein the alkane weight percentage is in the range of 30-70% with respect to the feedstock.

17. The process as claimed in claim 4, wherein the alkene is a mixture of butenes and the oligomer product is a mixture of octenes and dodecenes and the octene selectivity is up to 92%.

* * * * *